(12) United States Patent
Spitz (10) Patent No.: US 7,571,747 B2
(45) Date of Patent: Aug. 11, 2009

(54) SYRINGE FILLING APPARATUS

(76) Inventor: Gregory A. Spitz, 3000 Ogden Ave., Suite E101, Aurora, IL (US) 60504

( * ) Notice: Subject to any disclaimer, the term of this patent is extended or adjusted under 35 U.S.C. 154(b) by 553 days.

(21) Appl. No.: 11/328,045

(22) Filed: Jan. 9, 2006

(65) Prior Publication Data

US 2007/0161959 A1    Jul. 12, 2007

(51) Int. Cl.
B65B 3/04        (2006.01)
A61B 19/00       (2006.01)

(52) U.S. Cl. .............................. 141/2; 141/21; 141/244; 141/318; 604/414

(58) Field of Classification Search ............. 141/2, 141/21, 22, 23, 25, 27, 31, 114, 237, 242, 141/244, 245, 247, 318, 378; 604/411–414
See application file for complete search history.

(56) References Cited

U.S. PATENT DOCUMENTS

| | | | |
|---|---|---|---|
| 3,498,342 A * | 3/1970 | Sanderson | 141/238 |
| 3,662,517 A | 5/1972 | Tafcher et al. | |
| 3,734,147 A | 5/1973 | Borutta et al. | |
| 3,807,467 A * | 4/1974 | Tascher et al. | 141/375 |
| 3,833,030 A | 9/1974 | Waldbauer, Jr. et al. | |
| 3,855,868 A * | 12/1974 | Sudvaniemi | 73/863.32 |
| 4,489,766 A | 12/1984 | Montada | |
| 4,501,306 A | 2/1985 | Chu et al. | |
| 4,842,581 A * | 6/1989 | Davis | 604/38 |
| 4,846,797 A | 7/1989 | Howson et al. | |
| 4,978,336 A * | 12/1990 | Capozzi et al. | 604/82 |
| 5,179,983 A | 1/1993 | Cordner, Jr. et al. | |
| 5,253,785 A * | 10/1993 | Haber et al. | 222/43 |
| 5,329,976 A | 7/1994 | Haber et al. | |
| 5,385,559 A | 1/1995 | Mannix | |
| 5,542,760 A | 4/1997 | Halbich | |
| 5,620,422 A | 4/1997 | Halbich | |
| 5,647,409 A | 7/1997 | Christ et al. | |
| 5,716,345 A | 2/1998 | Halbich | |
| 5,844,457 A | 12/1998 | Eckroth et al. | |

(Continued)

FOREIGN PATENT DOCUMENTS

EP        1236644 A1    9/2002

(Continued)

Primary Examiner—Timothy L Maust
Assistant Examiner—Nicolas A Arnett
(74) Attorney, Agent, or Firm—Cardinal Law Group (57) ABSTRACT

The present invention relates to devices and methods for the filling syringes. One medical apparatus in accordance with the present invention include a body member for releasably holding syringe barrels and an actuator apparatus slidably mounted on the body member to engage syringe plungers to cause the syringe plunger to be retracted. A fluid delivery apparatus is releasably mounted to the body member. The fluid delivery apparatus has an inlet port and a plurality of outlet ports. The inlet port is in fluid communication with each of the plurality of outlet ports. One method for filling a plurality of syringes in accordance with the present invention includes the steps of mounting a plurality a syringes to a syringe holding member and connecting a fluid delivery apparatus to the syringe holding member to mate with each of the tips of the syringe barrels. The method also includes the steps of placing an inlet port of the fluid delivery apparatus in a fluid and moving an actuator apparatus to retract the syringe plungers to cause fluid to enter the syringe barrels.

3 Claims, 9 Drawing Sheets

U.S. PATENT DOCUMENTS

| | | |
|---|---|---|
| 5,911,252 A | 6/1999 | Cassel |
| 6,685,693 B1 | 2/2004 | Casso |
| 6,915,823 B2 | 7/2005 | Osborne et al. |
| 7,117,901 B2 * | 10/2006 | Martinell Gisper-Sauch et al. ............................ 141/2 |
| 2001/0018937 A1 | 9/2001 | Nemoto |
| 2002/0020459 A1 * | 2/2002 | Baldwin et al. ................ 141/11 |
| 2006/0118199 A1 * | 6/2006 | Yamazaki .................... 141/130 |
| 2007/0186992 A1 * | 8/2007 | Bullen ......................... 141/65 |

FOREIGN PATENT DOCUMENTS

| | | |
|---|---|---|
| WO | WO/2004/108533 | 12/2004 |

* cited by examiner

SYRINGE FILLING APPARATUS

TECHNICAL FIELD

The present invention generally relates to medical apparatus. More particularly, the present invention relates to apparatus and methods for filling medical syringes.

BACKGROUND

Many medical procedures require injecting a fluid into a patient using a syringe. In certain medical procedures, multiple syringes may be needed to administer the fluid into the patient. For example, in treating varicose vein using "sclerotherapy", multiple injections of a sclerosing solution are administrated to the patient. In this procedure, 40-60 syringes may be utilized to inject the solution during a treatment session. Before the syringes can be used to inject the solution, the syringes must initially be filled. Once all of the syringes are filled, the syringes can be utilized to deliver the solution to the patient.

One method of obtaining a filled syringe is to purchase syringes that have been pre-loaded with the desired fluid. However, this method has several disadvantages. First, pre-loaded syringes having the desired fluid may not be readily available. Second, if the syringe is available, it may not have the desired amount of fluid and may be relatively expensive. For these and other reasons, pre-loaded syringes may not be desirable.

An alterative method of filing syringes involves manually filling the syringes. This method involves manually inserting the needle of each syringe, one at a time, into a sealed vial containing the fluid. Once the needle is inserted into the container, the syringe plunger is withdrawn until the syringe barrel is filled with the desired amount of fluid. The operation is repeated for each syringe until the number of desired syringes are filled. However, manually filling multiple syringes can be time consuming and labor intensive. Further, the needle of the syringe may be damaged when the needle is inserted into the sealed container, requiring the needle to be replaced.

SUMMARY OF THE INVENTION

In view of the above, the present invention provides medical apparatus and methods for filling a plurality of syringes. The medical apparatus and methods allow multiple syringes to be easily and quickly filled at the same time. The medical apparatus and methods also allow medical practitioners to quickly fill any additional syringes needed during a treatment of a patient. As a result, medical practitioners can reduce the amount of time spent for filling syringes, thereby reducing labor costs for the medical treatment.

The medical apparatus further allows medical practitioners to fill a number of syringes with approximately the same amount of liquid. The medical apparatus also fills multiple syringes without the need to insert the syringe needles into a sealed container of fluid, thereby avoiding damage to the syringe needles. In addition, the medical apparatus is portable allowing it to be used in various treatment rooms in a medical facility and is less expensive than electronic automatic syringe fillers.

One medical apparatus in accordance with the present invention includes a body member for releasably holding syringe barrels. An actuator apparatus is slidably mounted on the body member to engage the syringe plungers to cause the syringe plunger to be retracted. A fluid delivery apparatus is releasably mounted to the body member. The fluid delivery apparatus has an inlet port and a plurality of outlet ports. The inlet port is in fluid communication with each of the plurality of outlet ports.

One method for filling a plurality of syringes in accordance with the present invention includes the steps of mounting a plurality a syringes to a syringe holding member and connecting a fluid delivery apparatus to the syringe holding member to mate with each of the tips of the syringe barrels. The method also includes the steps of placing an inlet port of the fluid delivery apparatus in a fluid and moving an actuator apparatus to retract the syringe plungers to cause the fluid to enter the syringe barrels.

The invention, together with further attendant advantages, will best be understood by reference to the following detailed description of the presently preferred embodiments of the invention, taken in conjunction with the accompanying drawings. It is to be understood that both the foregoing general description and the following detailed description are exemplary and explanatory and are intended to provide further explanation of the invention as claimed.

BRIEF DESCRIPTION OF THE DRAWINGS

A preferred embodiment of the present invention will be described in detail below in connection with the drawings in which.

DESCRIPTION OF PREFERRED EMBODIMENTS

Before explaining the preferred embodiments in detail, it should be noted that the invention is not limited in its application or use to the details of construction and arrangement of parts illustrated in the accompanying drawings and description, because the illustrative embodiments of the invention may be implemented or incorporated in other embodiments, variations and modifications, and may be practiced or carried out in various ways. Furthermore, unless otherwise indicated, the terms and expressions employed herein have been chosen for the purpose of describing the preferred embodiments of the present invention for the convenience of the reader and are not for the purpose of limitation.

Figure 1:
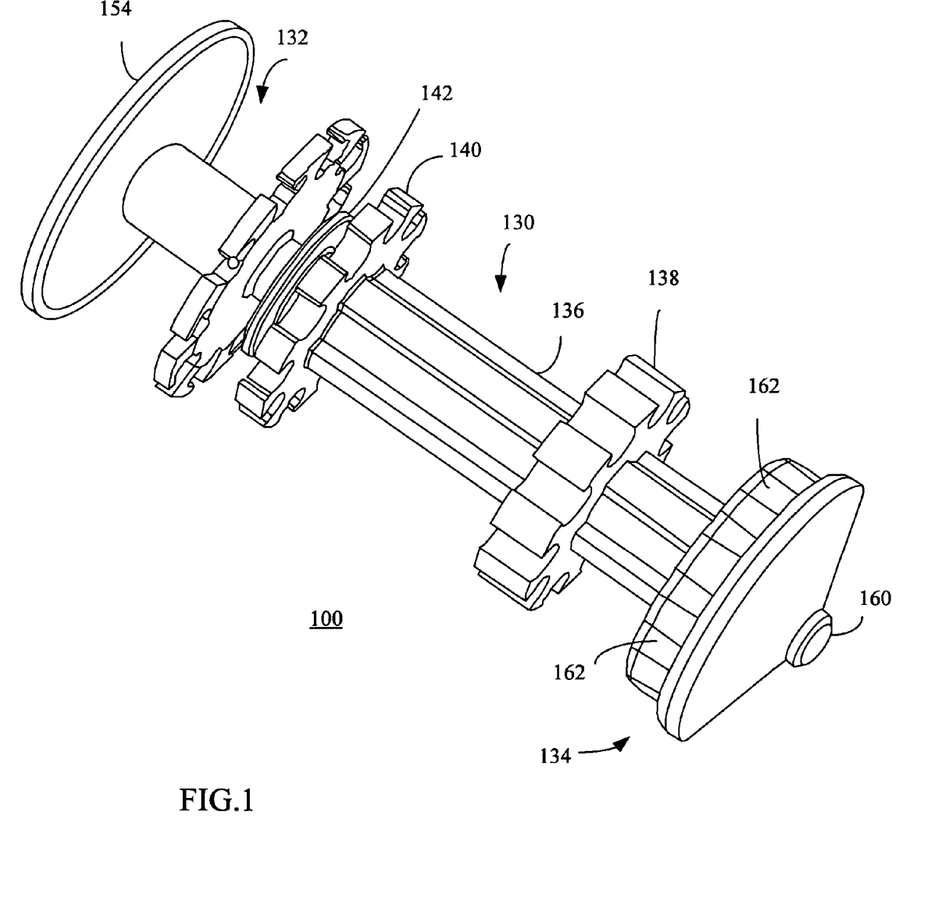
FIG. 1 is a perspective view of the medical apparatus in accordance with the present invention.
Figure 2:
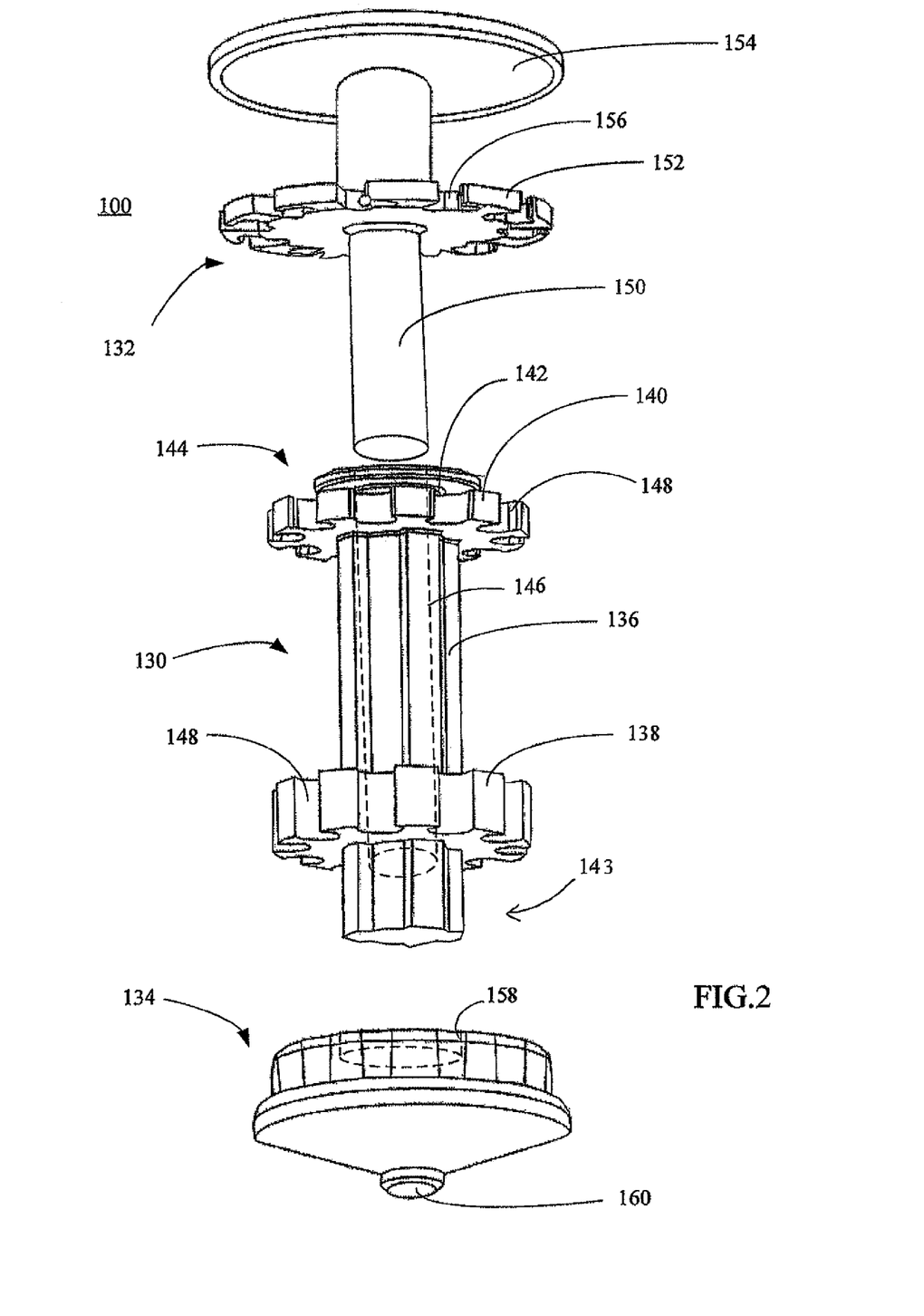
FIG. 2 is an exploded perspective view of the medical apparatus of FIG. 1.
Figure 3:
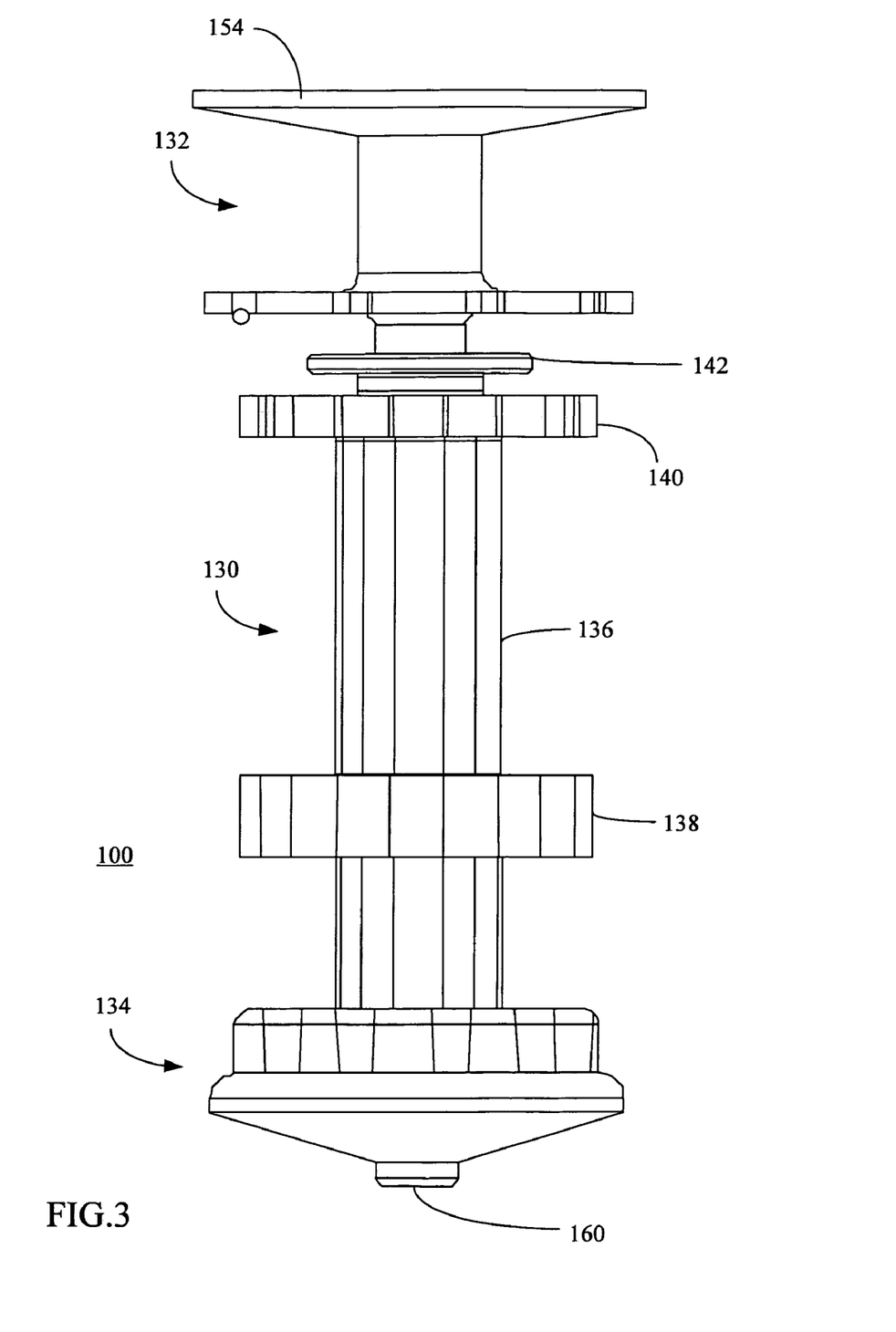
FIG. 3 is a side elevational view of the medical apparatus of FIG. 1.
Figure 4:
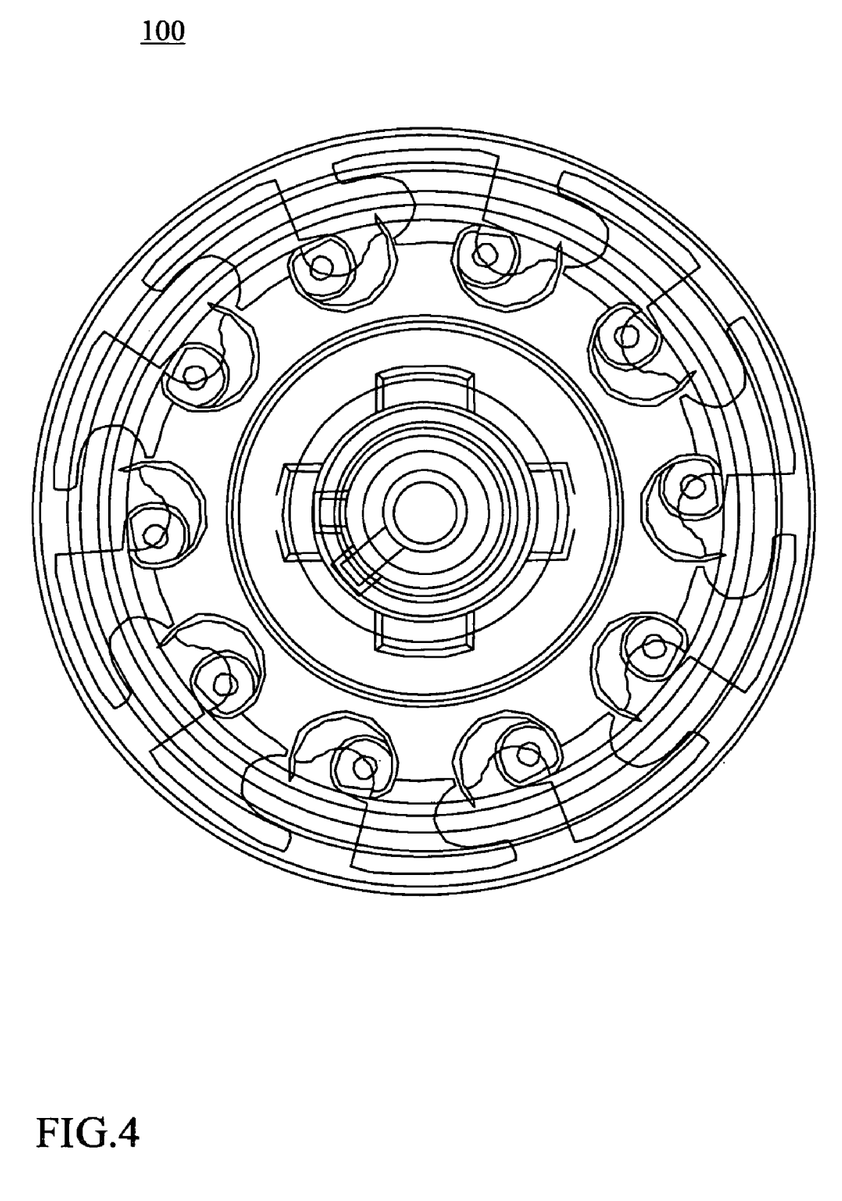
FIG. 4 is a bottom view of the medical apparatus of FIG. 1.

Referring now to the drawings in detail, and particularly to FIGS. 1-3, a preferred embodiment of a medical apparatus 100 for filling a plurality of syringes is illustrated. The medical apparatus 100 allows multiple syringes to be easily and quickly filled at the same time. As a result, medical practitioners can reduce the amount of time spent for filling syringes, thereby reducing labor costs for the medical treatment.

The medical apparatus 100 also allows medical practitioners to fill a number of syringes with approximately the same amount of liquid. In addition, the medical apparatus fills multiple syringes without the need to insert the needle of the syringe in a sealed container of fluid, thereby avoiding damage to the syringe needles. Further, the medical apparatus can be used if additional syringes need to be quickly filled during a treatment of a patient. The medical apparatus is portable allowing it to be used in various treatment places in a medical facility and is less expensive than electronic automatic fillers.

Figure 5:
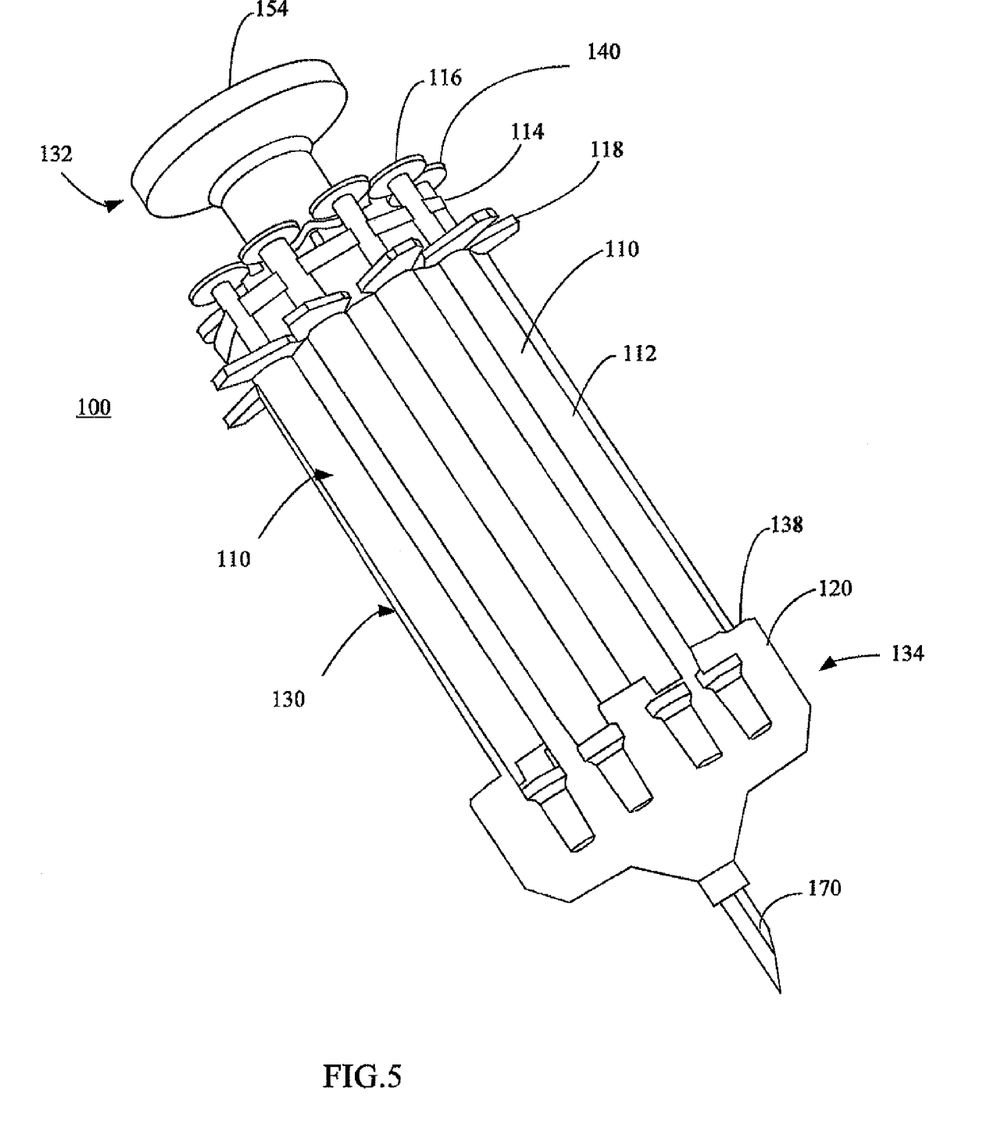
FIG. 5 is a perspective view of the medical apparatus of FIG. 1.

The medical apparatus 100 of FIG. 1 is utilized to fill a plurality of conventional syringes 110. As shown in FIG. 5, the syringes 110 generally include a syringe barrel 112 and a syringe plunger 114 movably disposed within the syringe barrel 112. The syringe plunger 114 has a rubber bulb (not shown) on one end and a plunger head 116 on the other end. The syringe barrel 112 surrounds the lower portion of the syringe plunger 114. The syringe barrel 112 has a flange 118 at the upper end and a nozzle or tip 120 at the other end. The tip 120 can be attached to a needle once the syringes are filled with fluid. It should be recognized that the syringes are conventional and are not part of the present invention.

Referring now to FIGS. 1-3, the medical apparatus 100 includes a syringe holder apparatus 130, an actuator apparatus 132, and a fluid delivery apparatus or hub 134. The syringe holder apparatus 130 is configured to receive and hold a plurality of syringes to be filled with fluid. As shown in FIG. 5, the syringe holder apparatus 130 can hold up to ten (10) syringes, but it will be recognized that the syringe holder apparatus can be configured to hold any suitable number of syringes. The syringe holder apparatus 130 can be constructed from nylon, Teflon, polyurethane, or polyethylene. It will be recognized that the syringe holder apparatus 130 can be made from a variety of other materials including, for example, polypropylene, polyamide, polyethylenterephthalate, polyamide, other polymers and polycarbonates as well as other suitable forms of plastic.

The syringe holder apparatus 130 of the medical apparatus 100 generally includes an elongated member 136, first and second retaining members or collars 138 and 140, and a stop member 142. The elongated member 136 preferably has a substantially circular cross-section, but may have any suitable cross-section, such as a square or an elliptical cross-section. The elongated member 136 of the syringe holder apparatus 130 preferably includes a first end 143, a second end 144, and an aperture or bore 146 extending axially from its second end 144. The aperture 146 of the elongated member 136 allows the syringe holder apparatus 130 to be slidably mounted to the actuator apparatus 132 as further described below. The first end 143 of the elongated member 136 is configured to releasably mount to the fluid delivery apparatus 134.

The first and second retaining members 138 and 140 of the syringe holder apparatus 130 are mounted to the elongated member 136 at a pre-selected distance in order to securely hold the syringes during the filling process. The first retaining member 138 is mounted near the first end 143 of the elongated member 136 to releasably hold the upper portions of the syringe barrels, and the second retaining member 140 is attached near the second end 144 of the elongated member 136 to releasably hold the lower portions of the syringe barrels. As shown in FIG. 5, the syringe barrel 112 is disposed between the first and second retaining members 138 and 140. The spacing between the first and second retaining members 138 and 140 can be any suitable distance that is less than the length of the syringe barrel. It will be recognized that the syringe holder apparatus 130 may only have one retaining member or multiple retaining member to releasably hold the syringes to be filled.

The first and second retaining members 138 and 140 of the syringe holder apparatus 130 each have a plurality of recesses or slots 148 formed around its outer edge. The recesses 148 are adapted to receive and hold the syringe barrel. Preferably, the recesses 148 are sized to fit snugly around the syringe barrel, allowing a medical practitioner to easily and quickly attach or snap the syringe barrel to the syringe holder apparatus 130. It will be recognized that the recesses 148 can be configured to accommodate any suitable size syringe barrel and other mechanisms can be used to releasably hold the syringe barrels on the syringe holding member 130. For example, a clip or finger like member may be used to hold the syringe barrels onto the syringe holding member 130. The first and second retaining members 138 and 140 preferably have the same number of recesses that are in substantial alignment relative to the axis of the elongated member 136 of the syringe holding apparatus 130.

Figure 8:
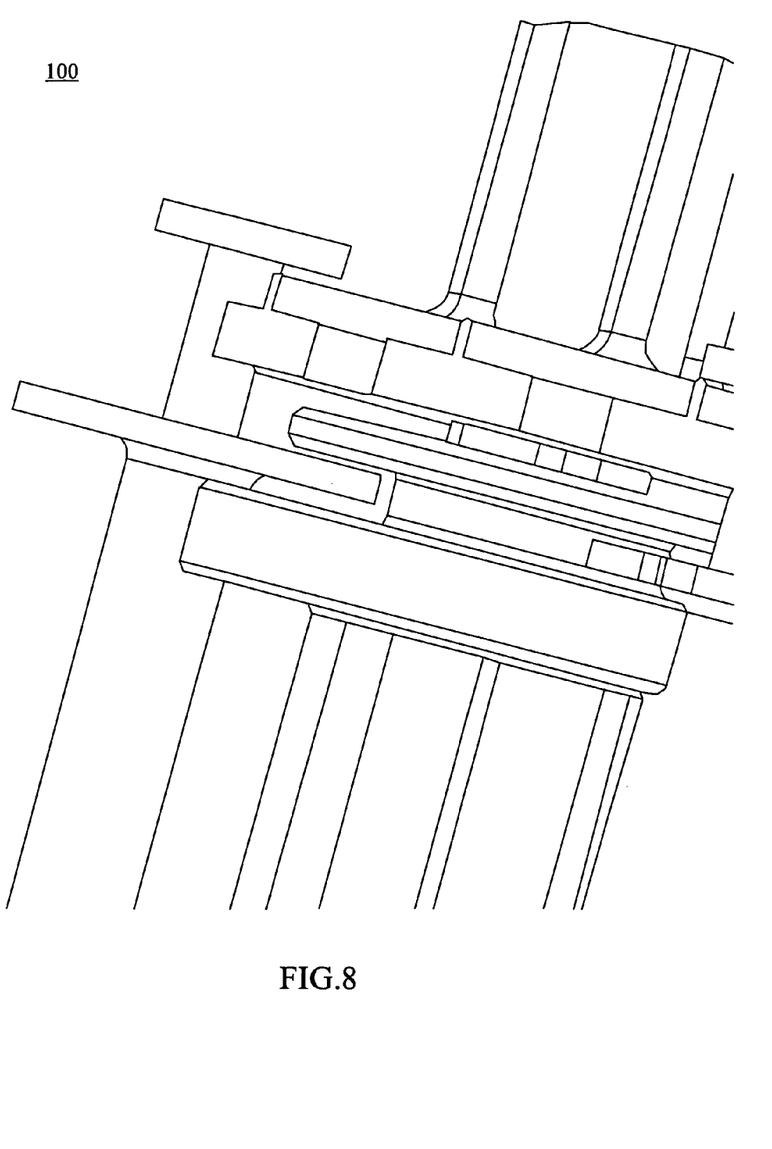
FIG. 8 is another fragmentary perspective view of the medical apparatus of FIG. 1.

The stop member 142 of the syringe holder apparatus 130 is mounted to the second end 144 of the elongated member 136. The stop member preferably is cylindrically shaped, but can have any suitable shape. The stop member 142 is mounted to position the actuator apparatus to engage the plunger heads of the syringes as shown in FIG. 8 and as further described below.

As shown in FIG. 2, the actuator apparatus 132 of the medical apparatus 100 generally includes an elongated shaft 150, a driver or retraction member 152 and a hand grip or knob 154. The actuator apparatus 132 is slidably mounted to the syringe holder apparatus 130 to allow the plungers of the syringes mounted on the syringe holder apparatus 130 to be retracted or extended in order to cause the fluid to be drawn into the syringe barrels.

The elongated shaft 150 of the actuator apparatus 132 is slidably positioned in the aperture 146 of the syringe holder apparatus 130. The elongated shaft 150 can be moved axially in the aperture 146 of the syringe holder apparatus 130 to allow the actuator apparatus 132 to be moved relative to the syringe holder apparatus 130. The elongated shaft 150 may also be rotated in the aperture 146 of the syringe plunger apparatus to allow the driver member 152 to interlock with the syringe plunger as further described below.

The drive member 152 of the actuator apparatus 132 is configured and positioned to engage with the plunger heads of the syringes to move or retract the syringe plungers when the actuator apparatus 132 is withdrawn. As a result, fluid is drawn through the fluid delivery member and into the syringes. The driver member 152 includes a plurality of recesses 156 to receive the shaft of the syringe plunger. The recesses 156 preferably have a larger diameter than the shaft of the syringe plunger so that the recesses 156 loosely receive the shaft of the syringe plunger. However, the recesses 156 have a smaller diameter than plunger head of the syringe in order to engage the plunger head upon movement of the drive member 152.

Figure 7:
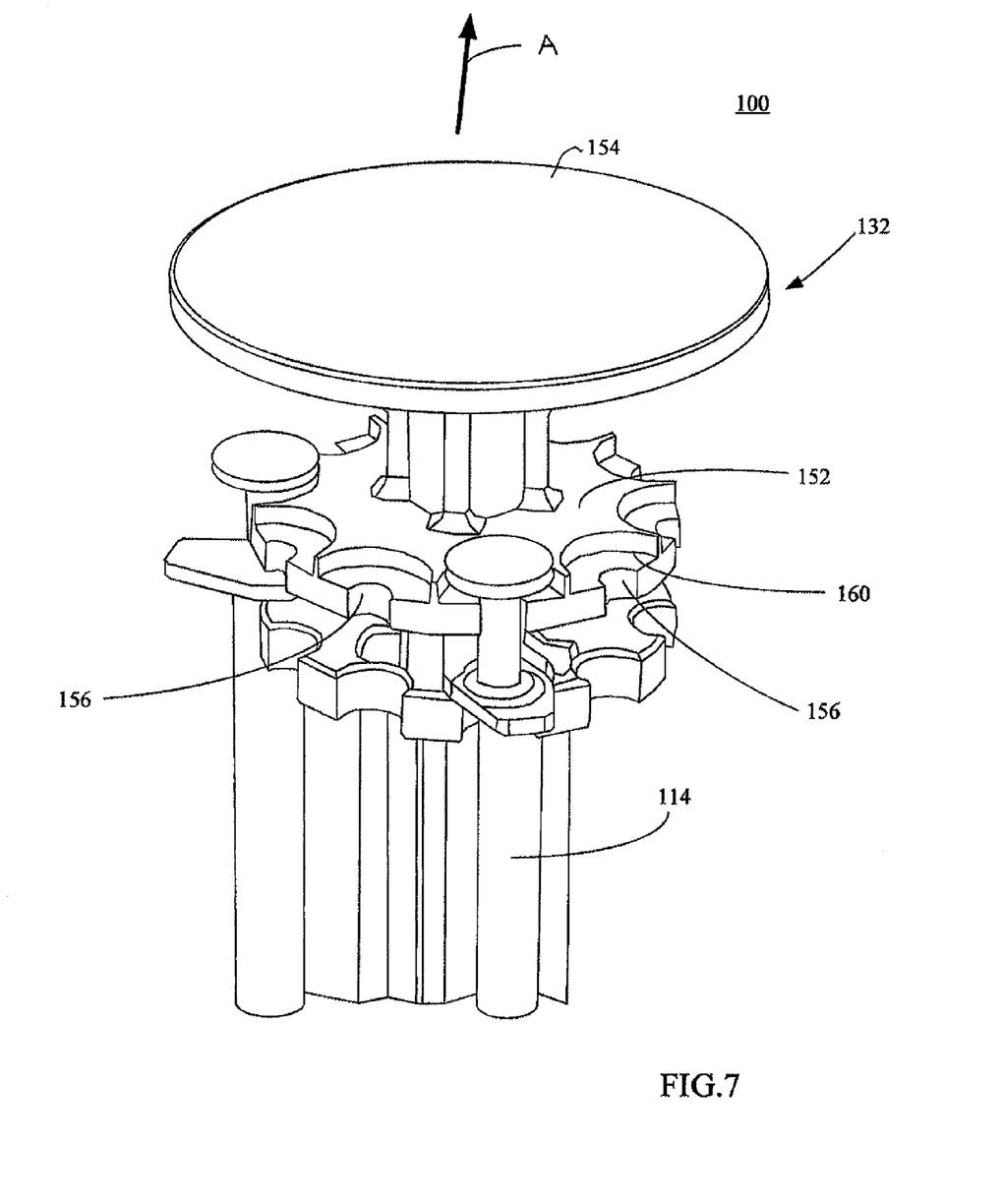
FIG. 7 is a fragmentary perspective view of the medical apparatus of FIG. 1.

As shown in FIGS. 1 and 7, the recesses 156 of the drive member 152 can be configured to interlock with the shaft of the syringe plunger when the actuator member is rotated clockwise. When the actuator apparatus 132 is moved in the direction of arrow A, the drive member 152 will engage the plunger head to move the syringe plunger and further movement will cause the extension of the syringe plunger. In an alternative embodiment shown in FIGS. 7 and 8, when the syringe barrel is mounted to the syringe holding member, the shaft of the syringe plungers 114 fit into the recesses of the retraction member and the plunger head 116 seats in an indentation or recess 160 of the drive member 152.

The hand grip 154 of the actuator apparatus 132 is substantially cylindrically shaped and is adapted to be grasped by a user or medical practitioner. It will be recognized that the hand grip 154 may be any suitable shape or size which allows it to be grasped by the user. The hand grip 154 allows a user to move the actuator apparatus 132 in an upwardly fashion to cause the drive member 152 to contact the plunger head of the syringe plunger. Once the drive member 152 contacts the plunger head and begins to move the syringe plunger, fluid to be drawn into the syringe barrel as further described below.

Referring now to FIGS. 1-3, the fluid delivery apparatus 134 of the medical apparatus 100 is releasably mounted to the first end 143 of the elongated member 136 of the syringe holder apparatus 130. The fluid delivery apparatus 134 allows fluid to be transported from a container of fluid into the syringe barrels that are mounted on the syringe holder apparatus 130. The fluid delivery apparatus 134 can be constructed from nylon, Teflon, polyurethane, or polyethylene. It will be recognized that the fluid delivery apparatus 134 can be made from a variety of other materials including, for example, polypropylene, polyamide, polyethylenterephthalate, polyamide, other polymers and polycarbonates as well as other suitable forms of plastic.

The fluid delivery apparatus 134 includes a bore 158, an inlet port 160 and a plurality of outlet ports 162. The bore 158 is configured so that the fluid delivery apparatus 134 can be releasably mounted to the first end 143 of the elongated member 136 of the syringe holder apparatus 132. The bore 158 can be any suitable shape to mate with the configuration of the first end 143 of the elongated member 136.

Figure 9:
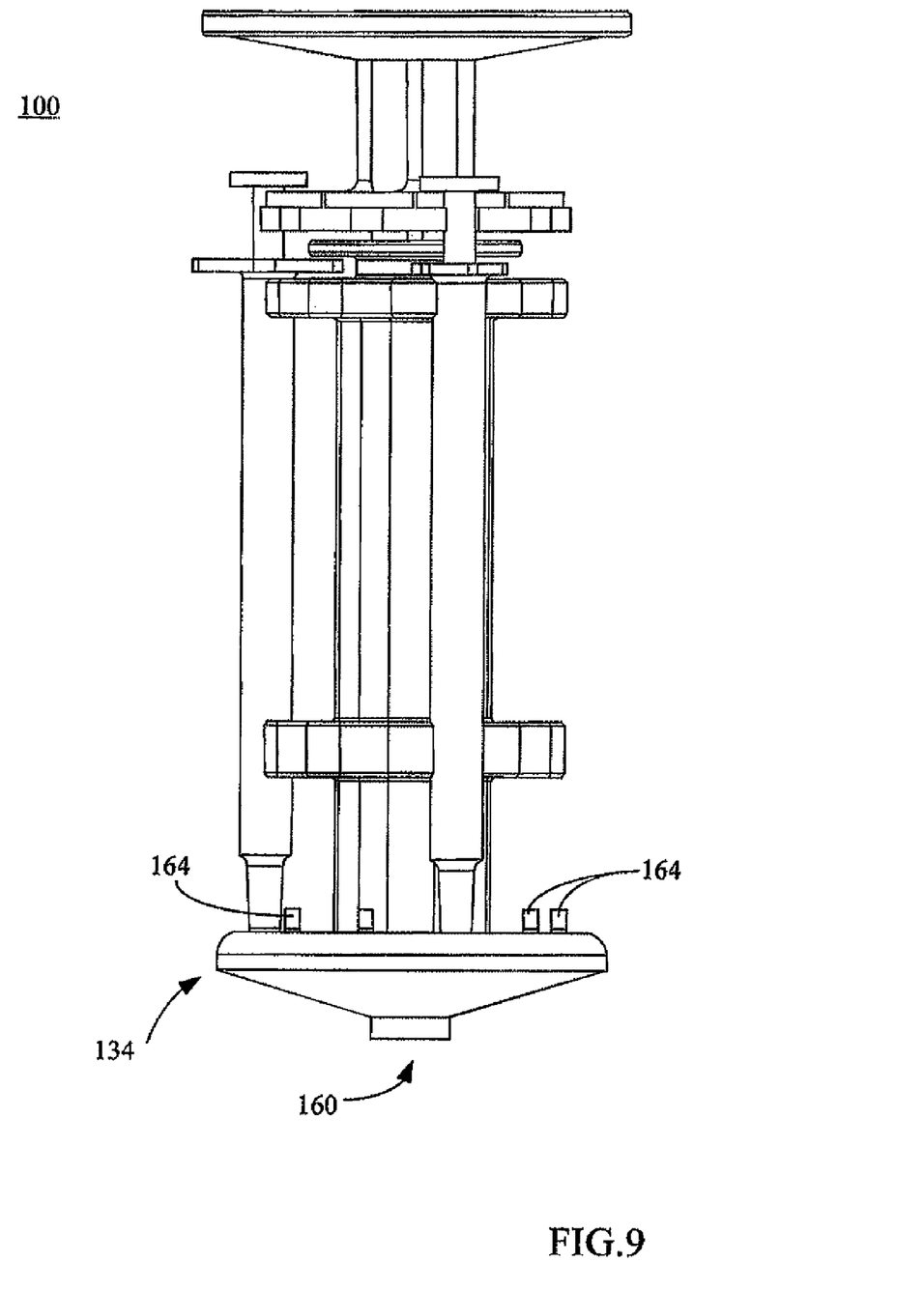
FIG. 9 is a side view of another embodiment of a medical apparatus in accordance with the present invention.

As shown in FIG. 1, the outlet ports 162 of the fluid delivery apparatus include a plurality of apertures formed in the upper surface of the fluid delivery apparatus 134. The apertures are sized to fit snugly around the tips of the syringe barrels. In an alternative embodiment shown in FIG. 9, the outlet ports 162 are formed by hollow sleeves 164 that extend outwardly from the upper end of the fluid delivery apparatus 134. The hollow sleeves 164 fit within the hole in the tip of the syringe barrel.

Figure 6:
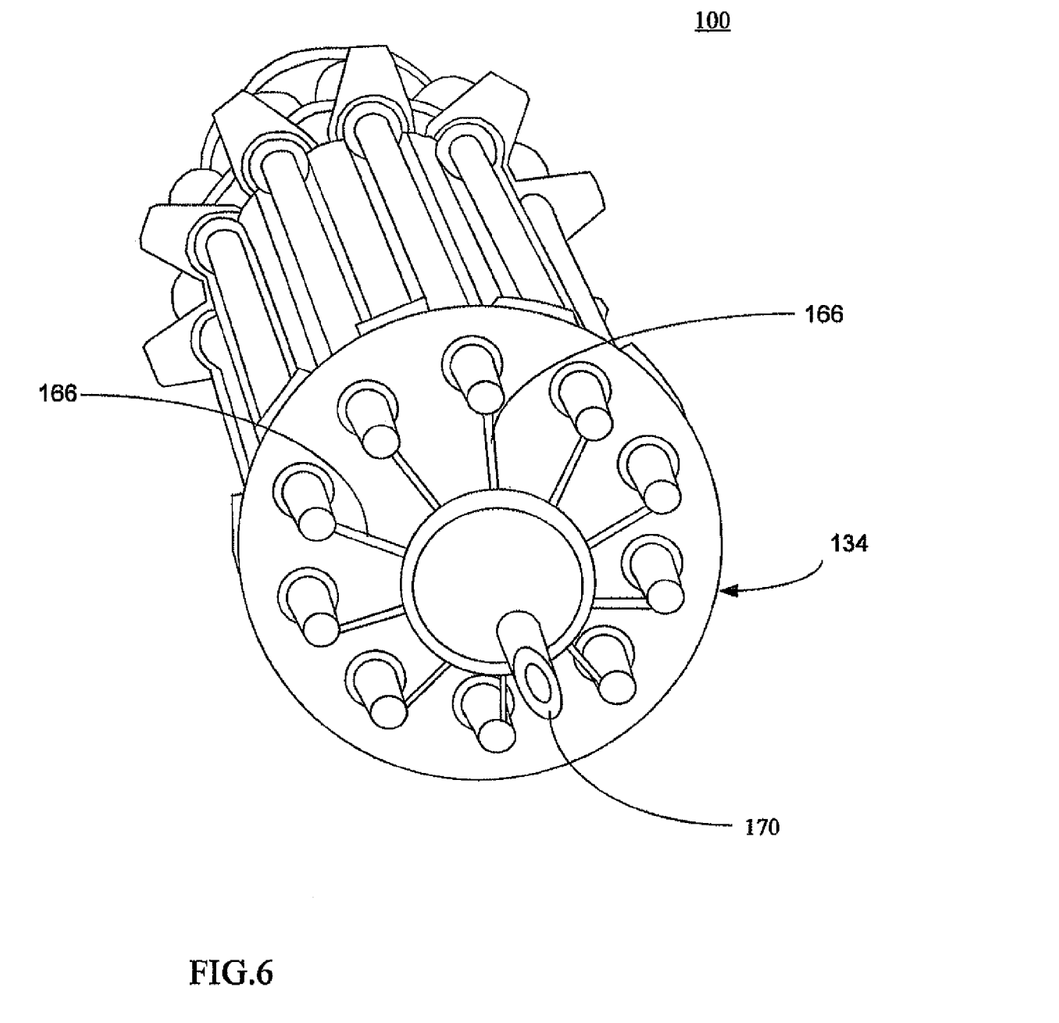
FIG. 6 is another perspective view of the medical apparatus of FIG. 1

As shown in FIG. 6, a delivery conduit or pathway 166 extends from each outlet port 162 to the inlet port 160 of the fluid delivery apparatus 134. The delivery conduits 166 allow fluid to flow from the inlet port 160 to each of the outlet ports 162. A nozzle 170 or tube can be connected to the inlet port 160 to facilitate obtaining fluid.

The method of filling a plurality of syringes with the medical apparatus 100 of FIG. 1 will now be described. Initially, a medical practitioner places a plurality of syringes on the syringe holding apparatus 130 with the actuating apparatus 132 in its retracted or closed position. In this position, the plunger head will rest against the drive member 152 of the actuating apparatus 132.

A container having a desired fluid is opened or prepared, and a nozzle attached to the inlet port 160 of the medical apparatus 100 is placed in the fluid. It will be recognized that the inlet port 160 may be connected to a tube that can be inserted into the container.

Once the nozzle is placed in the fluid, the medical practitioner grasps the hand grip 154 of the actuator apparatus 132 and pulls it in an upward direction. As the actuator apparatus 132 moves upwardly, the drive member 152 of the actuator apparatus 132 engages the plunger heads of the syringe plungers causing the syringe plungers to be extended or retracted. As the syringe plungers are retracted, fluid is drawn through the inlet port and through the outlet ports via the delivery conduits. The fluid then travels through the tips of the syringes and into each of the syringe barrels.

Once the desired amount of liquid is drawn into each of the syringe barrel, the medical practitioner will stop retracting the actuator member 132. Once the syringes are filled, the medical practitioner can remove the syringes from the syringe holding member and use the syringes to inject fluid into a patient. This process can be repeated until the desired number of syringes are filled.

The medical apparatus and methods described above allow a plurality of syringes to be quickly and easily filled at the same time. As a result, medical practitioners can reduce the amount of time spent for filling syringes, thereby reducing labor costs for the medical treatment. The medical apparatus also fills multiple syringes without the need to insert the needle of the syringe in the sealed container, thereby avoiding damage to the syringe needles.

In addition, the medical apparatus can be used to quickly fill syringes if additional syringes need to be filled during a treatment of a patient. Further, the medical apparatus is portable allowing it to be used in various treatment places in a medical facility. The medical apparatus is also less expensive than electronic automatic syringe fillers.

Although the present invention has been described in detail by way of illustration and example, it should be understood that a wide range of changes and modifications can be made to the preferred embodiments described above without departing in any way from the scope and spirit of the invention. Thus, the described embodiments are to be considered in all respects only as illustrative and not restrictive, and the scope of the invention is, therefore, indicated by the appended claims rather than the foregoing description. All changes that come within the meaning and range of equivalency of the claims are to be embraced within their scope.

What is claimed is:

1. A method for filling a plurality of syringes with a fluid, each of the syringes having a syringe barrel and a syringe plunger movably disposed within the syringe barrel, the method comprising the steps of:
   mounting the plurality of syringes to an elongate syringe holding member, the elongate holding member having a central axial aperture;
   connecting a fluid connecting member to the syringe holding member to mate with each tip of the syringe barrels;
   placing an inlet port of the fluid connecting member in a fluid; and
   moving an actuator apparatus slidably mounted within the central axial aperture of the syringe holding member to retract the syringe plungers to cause fluid to enter the syringe barrels.

2. The method of claim 1 farther comprising the step of moving the actuator apparatus until a desired amount of fluid is filled in the syringe barrel.

3. The method of claim 2 further comprising the step of removing the syringes from the syringe holding member.

* * * * *